United States Patent [19]
Charette et al.

[11] Patent Number: 5,759,815
[45] Date of Patent: Jun. 2, 1998

[54] PRODUCTION OF PLATELET DERIVED GROWTH FACTOR (PDGF) AN MUTEINS THEREOF

[75] Inventors: Marc F. Charette, West Roxbury; Zita A. Babickas, Natick; Hermann Oppermann, Medway, all of Mass.

[73] Assignee: Creative BioMolecules, Inc., Hopkinton, Mass.

[21] Appl. No.: 686,550

[22] Filed: May 6, 1991

Related U.S. Application Data

[62] Division of Ser. No. 155,066, Feb. 11, 1988, abandoned.

[51] Int. Cl.⁶ ............................................. C12N 15/18
[52] U.S. Cl. .................. 435/69.4; 435/252.3; 530/399; 530/412
[58] Field of Search .......................... 935/60, 49, 51; 530/409, 300, 412, 350, 395, 399; 514/12; 435/69.4, 252.3

[56] References Cited

U.S. PATENT DOCUMENTS

| | | | |
|---|---|---|---|
| 4,350,687 | 9/1982 | Lipton et al. | 424/177 |
| 4,431,739 | 2/1984 | Riggs | 435/253 |
| 4,479,896 | 10/1984 | Antoniades | 260/112 B |
| 4,530,787 | 7/1985 | Shaked et al. | 260/112 R |
| 4,572,798 | 2/1986 | Koths et al. | 260/112 R |
| 4,694,073 | 9/1987 | Bentle et al. | 530/399 |
| 4,711,847 | 12/1987 | König et al. | 435/70 |
| 4,766,073 | 8/1988 | Murray et al. | 435/172.3 |
| 4,782,139 | 11/1988 | DiMarchi et al. | 530/407 |
| 4,801,542 | 1/1989 | Murray et al. | 435/172.3 |
| 4,845,075 | 7/1989 | Murray et al. | 514/12 |
| 4,849,407 | 7/1989 | Murray et al. | 514/12 |

FOREIGN PATENT DOCUMENTS

| | | |
|---|---|---|
| 0177957 | 4/1986 | European Pat. Off. . |
| 0224885 | 6/1987 | European Pat. Off. . |
| 2146335 | 4/1985 | United Kingdom . |
| WO 85/04413 | 10/1985 | WIPO . |
| 90/04035 | 4/1986 | WIPO . |
| WO 86/05809 | 10/1986 | WIPO . |

OTHER PUBLICATIONS

Antoniades et al., *Proc. Natl. Acad. Sci.*, 1809–1813 (1979).
Betsholtz et al. (1986) *Nature*, 320:695–699.
Devare et al., (1984) *Cell*, 36:43–49.
Derynck et al., (1985) *Nature*, 316:701–705.
Hannink et al., (1986) *J. Cell Biology*, 103(6)2311–2322.
Heldin et al., Platelet–derived Growth Factor: Purification and Partial Characterization, 76(8) *Proc. Natl. Acad. Sci. USA* USA 3722–26 (1979).
Josephs et al. (1984) *Science*, 225:636–639.
Johnsson et al., (1984) *The EMBO Journal*, vol. 3, No. 5 921–928.
Raines et al. (1982) Platelet–Derived Growth Factor, 257(9) *The Journal of Biological Chemistry*, 5154–60 (1982).
Martinet et al., (1987) *New England Journal of Medicine*.
Vogel et al., (1989) *Biochemistry* 28:2961–2966.
Wang et al., *J. Biological chemistry*, pp. 10645–10648 (1984).
Watlaufer, D. (1984) Methods in Enzymology, 107:301–304.
Bolstein et al. (1985) *Science* 229:1193–1201.
Bowie et al., (1990) *Science*, 247:1306–1310.
Brot et al. (1983) *Archieves of Biochemistry and Biophysics*, 73(i):271–281.
Hoppe et al. (1987) "Preparation of Biologically Active PDGF B from a Fusion Protein Express in *E. Coli*"abstract presented at Symposium on Growth Factors and Their Reactions. Sponsored by European School of Oncology.
Wane, Jean Y.J. & Lewis T. Williams. "Av–sisoncogene Protein Produced in Bacteria Competes for Platelet–Derived Growth Factor–Binding to Its Receptor." J. Biol. Chem 259:10645–10648, 1984.
Wetlaufer, D. "Nonenzymatic–Formation and Isomerization of Protein Disulfides" Methods in Enzymology 107:301–304, 1984.

*Primary Examiner*—Lorraine Spector
*Attorney, Agent, or Firm*—Testa, Hurwitz & Thibeault, LLP

[57] ABSTRACT

Native, analog, and mutein species of A and B chains of platelet derived growth factor are produced in prokaryotes, purified, combined, and modified in vitro to produce various active AA, AB, and BB PDGF dimers.

15 Claims, 29 Drawing Sheets

FIG. 1a

```
                                            50
           10         20         30         40
GAATTCATGTTCTATCGAAGAAGCGGTACCGGGCTGTTTGTAAAACTCGTAC
 E  F  M  S  I  E  E  A  V  P  A  V  C  K  T  R  T
EcoRI NlaIII  MboII+  BanI HpaII            RsaI
       TaqI           KpnI
                      NlaIV
                      RsaI 60         70         80         90     95
TGTTATCTACGAAATCCCGAGATCTCAGGTTGACCCGACGTCTGCTAACT
 V  I  Y  E  I  P  R  S  Q  V  D  P  T  S  A  N
           AvaI BglII    HincII AatII
                Sau3A    AhaII
                XhoI 105        115        125        135        145
TCCTGATCTCGGCCACCGTGTTGAAGTTAAACGTTGTACTGGTTGTTGT
 F  L  I  W  P  P  C  V  E  V  K  R  C  T  G  C  C
BalI DraIII                      RsaI
Sau3A HaeIII
      CfrI
```

FIG. 1

| FIG. 1a |
|---------|
| FIG. 1b |
| FIG. 1c |

```
       160            170           180           190           200
AACACCCTCGAGGCGTTAAATGTCAGCCGTCTCGTTCACCATCGATCTGT
 N  T  S  S  V  K  C  Q  P  S  R  V  H  H  R  S  V
    AvaI                          HphI-ClaI
    MnlI+                                Sau3A
    TaqI                                 TaqI
    XhoI 210           220           230     235      245
TAAAGTCGGCGAAAGTTGAATACGTTCGTAAGAAACCGAAACTTAAGGAAG
 K  V  A  K  V  E  Y  V  R  K  K  P  K  L  K  E
    FnuDII     XmnI                        AflII
    NruI 255     265       275           285           295
TTCAGGTTCGTCTGGAAGAACACCTGGAATGTGCATGCTACTACAAGC
 V  Q  V  R  L  E  E  H  L  E  C  A  C  T  T  S
          MboII+  EcoRII     SphIHhaI     Alu
                 ScrFI       HinPI        Hind
                             NlaIII
                             NspHI
```

FIG. 1b

```
          310        320        330        340        350
TTGAATCCGGACTACCGTGAGGAGGACACTGGTAGACCGGTGAATCTGG
 L  N  P  D  Y  R  E  E  D  T  G  R  P  R  E  S  G
 I  BspMII    MnlI-       AccI FnuDII
 III HpaII       MnlI          HinfI
  HinfI 360        370        385        395
TAAGAAACGTAAGCGTAAACGTCTGAAACCGACTTAAGGATCCGTCGACGTGCAG
                                                  (polylinker)
405                                      *  G  S
 K  K  R  K  R  K  R  L  K  P  T
                                      AflIIBamHI
                                         NlaIV
                                         Sau3A
                                         XhoII
```

Underscored amino acid sequence is that of an A chain of PDGF.
* signifies the end of the structural gene encoding the A chain.

```
         10         20         30         40         50
GAATTCATGTCTATCGAAGAAGCGGTACCGGCTGTTTGTAAAACTCGTAC
 E  F  M  S  I  E  E  A  V  P  A  V  C  K  T  R  T
EcoRINlaIII  MboII+ BanIHpaII                  RsaI
        TaqI        KpnI
                    NlaIV
                    RsaI 60         70         80         90        100
TGTTATCTACGAAATCCCGAGATCTCAGGTTGACCCGACGTCTGCTAACT
 V  I  Y  E  I  P  R  S  Q  V  D  P  T  S  A  N
            AvaIBglII      HincII AatII
                 DdeI             AhaII
                 Sau3A
                 XhoII 110        120        130        140        150
TCCTGATCTGGCCACCGTGTTGAAGTTAAACGTTACTGGTTGTTGTTGT
 F  L  I  W  P  P  C  V  E  V  K  R  C  T  G  C  C
BalIDraIII                                   RsaI
Sau3AHaeIII
    CfrI
```

FIG. 2

| FIG. 2a |
| FIG. 2b |
| FIG. 2c |

```
        160              170              180              190              200
AACCCTCGAGCCGTTAAATGTCAGCCGTCTCGTGTTCACCATCGATCTGT
 N  T  S  S  V  K  C  Q  P  S  R  V  H  H  R  S  V
   AvaI                          HphI-ClaI
   MnlI+                                 Sau3A
   TaqI                                  TaqI
   XhoI 210              220              230              240              250
TAAAGTCGCGAAAGTTGAATACGTTCGTAAGAAAACCGAAACTTAAGGAAG
 K  V  A  K  V  E  Y  V  R  K  K  P  K  L  K  E
   FnuDII      XmnI                        AflII
   NruI 260              270              280              290              300
TTCAGGTTCGTCTCTGGAAGAACACCTGGAATGTGCATGCTACTACAAGC
 V  Q  V  R  L  E  E  H  L  E  C  A  C  T  T  S
         MboII+  EcoRII           SphIHhaI        Alu
                 ScrFI                HinPI       Hind
                                      NlaIII
                                      NspHI
```

FIG. 2b

```
              310       320       330       340       350
         TTGAATCCGGACTACCGTGAGGAGGACACTGACGTCCGTTAA
          L  N  P  D  Y  R  E  E  D  T  D  V  R  *
         I  BspMII     MnlI-        AccI
         III HpaII          MnlI-
             HinfI
```

Underscored amino acid sequence is that of an A chain of PDGF.

\* signifies the end of the structural gene encoding the A chain.

```
        10         20         30         40         50
GAATTCATGTCTCTGGGCTCTCTGACTATTGCCGAACCGGCAATGATTGC
 E  F  M  S  L  G  S  L  T  I  A  E  P  A  M  I  A
EcoRI                              BglI 60         70         80         90        100
TGAATGCAAGACTCGTACCGAAGTCTTCGAGATCTCTCGTCTGATCG
 E  C  K  T  R  T  E  V  F  E  I  S  R  R  L  I
BsmI+                    BglII              ClaI
                                            PvuI 110        120        130        140        150
ATCGCACTAATGCCAACTTCCTGGTATGGCCGTGTGAGGTACAA
 D  R  T  N  A  N  F  L  V  W  P  P  C  V  E  V  Q
              BstXI 160        170        180        190        200
CGCTGCTCCGGGGTGTTGCAACAATCGTAACGTTCAATGTCGACCGACTCA
 R  C  S  G  C  N  N  R  N  V  Q  C  R  P  T  Q
                                          SalI 210        220        230        240        250
AGTCCAGCTGCGTCCGGTCCAAGTCCGCAAAATCGAGATTGTACGTAAGA
 V  Q  L  R  P  V  Q  V  R  K  I  E  I  V  R  K
 PvuII                                      SnaBI
```

| FIG. 3a |
|---------|
| FIG. 3b |

FIG. 3

```
         260            270            280            290            300
AACCGATCTTTAAGAAGGCCACTGTGTTACTCTGGAAGACCATCTGGCATGC
 K  P  I  F  K  K  A  T  V  T  L  E  D  H  L  A  C
                                              SphI 310            320            330            340            350
AAATGTGAGACTGTAGCGGCCGCACTGTCCAGTTACTTAAGCTTGGGATCC
 K  C  E  T  V  A  A  A  R  P  V  T  *           (poly-
            EagI              AflII               BamHI
            NotI                    HindIII 360
GTCGACCTGCAG
 linker)
SalI  Pst
```

Underscored amino acid sequence is that of a B chain of PDGF.
* signifies the end of the structural gene encoding the B chain.

FIG. 3b

```
                  10                   20                   30                   40                   50
TCTCTGGGCTCTCTGACTATTGCCGAACCGGCCGTGATTGCTGAATGCAA
 S  L  G  S  L  T  I  A  E  P  A  V  I  A  E  C  K
                              BglI   EagI               BsmI+
                                     XmaIII 60                   70                   80                   90                  100
GACTCGTACCGAAGTCTTCGAGATCTCTCGTCGTCTGATCGATCGCACTA
 T  R  T  E  V  F  E  I  S  R  R  L  I  D  R  T
                           BglII                ClaI
                                                PvuI 110                  120                  130                  140                  150
ATGCCAACTTCCTGGTATGGCCGCCGTGCGTCGAGGTACAGCGCTGCTCC
 N  A  N  F  L  V  W  P  P  C  V  E  V  Q  R  C  S
 BstXI                                          Eco47III 160                  170                  180                  190                  200
GGGTGTTGCAACAATCGTAACGTACAATGTCGACTCAAGTCCAGCT
 G  C  C  N  N  R  N  V  Q  C  R  P  T  Q  V  Q  L
                                                PvuII
```

FIG. 4a

| FIG. 4a |
|---------|
| FIG. 4b |

FIG. 4

```
         210       220       230       240       250
GCGTCCGGTCCAAGTCCGCAAAATCGAGATTGTACGTAAGAAACCGATCT
 R  P  V  Q  V  R  K  I  E  I  V  R  K  K  P  I
                                  SnaBI 260       270       280       290       300
TTAAGAAGGCCACTGTTACTCTAGAAGACCATCTGGCATGCAAATGTGAG
 F  K  K  A  T  V  T  L  E  D  H  L  A  C  K  C  E
                      XbaI              SphI 310       320       330
ACTGTAGCGGCCGCACGTCCAGTTACTTAAGCTT
 T  V  A  A  A  R  P  V  T  *  A
       EagI         AflII
       NotI              HindIII
       XmaIII
```

\* signifies the end of the structural gene encoding the ser1-

```
         10                 20                 30                 40                 50
TCTCTGGCTCTCTCTGACTATTGCCGAACCGGCCATGATTGCTGAATGCAA
 S  L  G  S  L  T  I  A  E  P  A  M  I  A  E  C  K
                               BglI                    BsmI+

60                 70                 80                 90                100
GACTCGTACCGAAGTCTTCGAGATCTCTCGTCGTCTGATCGATGCACTA
 T  R  T  E  V  F  E  I  S  R  R  L  I  D  R  T
                   BglII                  ClaI
                                          PvuI 110                120                130                140                150
ATGCCAACTTCCTGGTATGGCCGCCGTGCGAGGTACAGCGCTGCTCC
 N  A  N  F  L  V  W  P  P  C  V  E  V  Q  R  C  S
    BstXI                                      Eco47III 160                170                180                190                200
GGGTGTTGCAACAATCGTAACGTACAAATGTCGTCCGACTCAAGTCCAGCT
 G  C  C  N  N  R  N  V  Q  C  R  P  T  Q  V  Q  L
                                                PvuII 210                220                230                240                250
GCGTCCGGTCCAAGTCCGCAAAATCGAGATTGTACGTAAGAAACCGATCT
 R  P  V  Q  V  R  K  I  E  I  V  R  K  K  P  I
                                          SnaBI
```

| FIG. 5a |
|---|
| FIG. 5b |

```
                           260           270          280           290           300
                   TTAAGAAGGCCACTGTTACTCTAGAAGACCATCTGGCATGCAAATGTGAG
                    F  K  K  A  T  V  T  L  E  D  H  L  A  C  K  C  E
                                         XbaI              SphI 310           320          330
                   ACTGTAGCGGCCCGCACGTCCAGTTACTTAAGCTT
                    T  V  A  A  A  R  P  V  T  *  A
                        EagI              AflII
                        NotI              HindIII
                        XmaIII
```

\* signifies the end of the structural gene encoding the ser1 B chain mutein.

FIG. 5b

```
         10              20              30              40           50
GCTCTGGGCTCTCTGACTATTGCCGAACCGGCCATGATTGCTGAATGCAA
 A  L  G  S  L  T  I  A  E  P  A  M  I  A  E  C  K
                     BglI                        BsmI+

60              70              80              90          100
GACTCGTACCGAAGTCTCTTCGAGATCTCTCGTCTGATCGATCGCACTA
 T  R  T  E  V  F  E  I  S  R  R  L  I  D  R  T
                          BglII             ClaI
                                            PvuI 110             120             130             140          150
ATGCCAACTTCCTGGTATGGCCGCCGTGCGTCGAGGTACAGCGCTGCTCC
 N  A  N  F  L  V  W  P  P  C  V  E  V  Q  R  C  S
       BstXI                                 Eco47III 160             170             180             190          200
GGGTGTTGCAACAATCGTAACGTACAATGTCGTCCGACTCAAGTCCAGCT
 G  V  C  N  N  R  N  V  Q  C  R  P  T  Q  V  Q  L
                                                PvuII
```

FIG. 6a

| FIG. 6a |
|---------|
| FIG. 6b |

FIG. 6

```
          210       220        230       240        250
GCGTCCGGTCCAAGTCCGCAAAATCGAGATTGTACGTAAGAAACCGATCT
 R  P  V  Q  V  R  K  K  I  E  I  V  R  K  K  P  I
                                 SnaBI 260       270        280       290        300
TTAAGAAGGCCACTGTTACTCTAGAAGACCATCTGGCATGCAAATGTGAG
 F  K  K  A  T  V  T  L  E  D  H  L  A  C  K  C  E
                     XbaI                  SphI 310       320        330
ACTGTAGCGGCCGCACGTCCAGTTACTTAAGCTT
 T  V  A  A  A  R  P  V  T  *  A
      EagI              AflII
      NotI                   HindIII
      XmaIII
```

\* signifies the end of the structural gene encoding the ala₁-met₁₂ B chain mutein.

FIG. 6b

```
         10                  20                  30                  40                  50
GCTCTGGGCTCTCTGACTATTGCCGAACCGGCCGTGATTGCTGAATGCAA
 A  L  G  S  L  T  I  A  E  P  A  V  I  A  E  C  K
                            BglI EagI              BsmI+
                                 XmaIII 60                  70                  80                  90                 100
GACTCGTACCGAAGTCTTCGAGATCTCTCGTCGTCTGATCGATCGCACTA
 T  R  T  E  V  F  E  I  S  R  R  L  I  D  R  T
                   BglII                    ClaI
                                            PvuI 110                 120                 130                 140                 150
ATGCCAACTTCCTGGTATGGCCGCCGTGCGTCGAGGTACAGCGCTGCTCC
 N  A  N  F  L  V  W  P  P  C  V  E  V  Q  R  C  S
            BstXI                              Eco47III 160                 170                 180                 190                 200
GGGTGTTGCAACAATCGTAACGTACAATGTCGTCCGACTCAAGTCCAGCT
 G  C  C  N  N  R  N  V  Q  C  R  P  T  Q  V  Q  L
                                                PvuI
```

FIG. 7a

| FIG. 7a |
|---------|
| FIG. 7b |

FIG. 7

```
              210       220       230       240       250
      GCGTCCGGTCCAAGTCCGCAAAATCGAGATTGTACGTAAGAAACCGATCT
        R  P  V  Q  V  R  K  I  E  I  V  R  K  K  P  I
                                     SnaBI 260       270       280       290       300
      TTAAGAAGGCCACTGTTACTCTAGAAGACCATCTGGCATGCAAATGTGAG
        F  K  K  A  T  V  T  L  E  D  H  L  A  C  K  C  E
                           XbaI               SphI 310       320       330
      ACTGTAGCGGCCGCACGTCCAGTTACTTAAGCTT
        T  V  A  A  A  R  P  V  T  *  A
           EagI                AflII
           NotI                   HindIII
           XmaIII
```

\* signifies the end of the structural gene encoding the ala1-val12 B chain mutein.

FIG. 7b

```
          10        20        30        40        50
AATATTCTGAAATGAGCTGTTGACAATTAATCATCGAACTAGTTAACTAG
SspI
Trp-promoter/operator -->

60        70        80        90       100
TACGCAAGTTCTCGTAAAAAGGGTATCGACAATGAAAGCAATTTTCGTAC
                                  M   K   A   I   F   V
                                : --> modified LE 110       120       130       140       150
TGAAAGGTTCACTGGACAGAGATCTGGACTCTCGTCTGGATCTGGACGTT
  L   K   G   S   L   D   R   D   L   D   S   R   L   D   L   D   V
leader peptide         BglII 160       170       180       190       200
CGTACCGACCACAAAGACCTGTCTGATCACCTGGTTCTGGTCGACCTGGC
  R   T   D   H   K   D   L   S   D   H   L   V   L   V   D   L   A 210       220       230       240       250
TCGTAACGACCTGGCTCGTATCGTTACTCCCGGGTCTCGTTACGTTGCGG
  R   N   D   L   A   R   I   V   T   P   G   S   R   Y   V   A 260
ATCTGGAATTCATG
  D   L   E   F   M
      EcoRI   : --> gene for PDGF
```

FIG. 8

| | |
|---|---|
| Glioma | S I E E A V P A V C K T R T V I Y |
| Endothelial | S I E E A V P A V C K T R T V I Y |
| Glioma (conti'.) | E I P R S Q V D P T S A N F L I H |
| Endo. (conti'.) | E I P R S Q V D P T S A N F L I W |
| Glioma (conti'.) | P P C V E V K R C T G C C N T S S |
| Endo. (conti'.) | P P C V E V K R C T G C C N T S S |
| Glioma (conti'.) | V K C Q P S R V H H R S V K V A K |
| Endo. (conti'.) | V K C Q P S R V H H R S V K V A K |
| Glioma (conti'.) | V E Y V R K K P K L K E V Q V R L |
| Endo. (conti'.) | V E Y V R K K P K L K E V Q V R L |
| Glioma (conti'.) | E E H L E C A C A T T S L N P D Y |
| Endo. (conti'.) | E E H L E C A C A T T S L N P D Y |
| Glioma (conti'.) | R E E D T G R P R E S G K K R K R |
| Endo. (conti'.) | R E E D T D V R M |
| Glioma (conti'.) | K R L K P T |

FIG. 10

E68 (Ala₁-Met₁₂)
  A L G S L T I A E P A M I A E C K T R T E V
E67 (Ala₁-Val₁₂)
  A L G S L T I A E P A V I A E C K T R T E V
E71 (Ser₁-Met₁₂)
  S L G S L T I A E P A M I A E C K T R T E V
E75 (Ser₁-Val₁₂)
  S L G S L T I A E P A V I A E C K T R T E V

E68 (conti'.)
  F E I S R R L I D R T N A N F L V W P P C V E
E67 (conti'.)
  F E I S R R L I D R T N A N F L V W P P C V E
E71 (conti'.)
  F E I S R R L I D R T N A N F L V W P P C V E
E75 (conti'.)
  F E I S R R L I D R T N A N F L V W P P C V E E68 (conti'.)  V Q R C S G C C N N R N V Q C R P T Q V Q L R
E67 (conti'.)  V Q R C S G C C N N R N V Q C R P T Q V Q L R
E71 (conti'.)  V Q R C S G C C N N R N V Q C R P T Q V Q L R
E75 (conti'.)  V Q R C S G C C N N R N V Q C R P T Q V Q L R E68 (conti'.)  P V Q V R K K I E I V R K K P I F K K A T V T
E67 (conti'.)  P V Q V R K K I E I V R K K P I F K K A T V T
E71 (conti'.)  P V Q V R K K I E I V R K K P I F K K A T V T
E75 (conti'.)  P V Q V R K K I E I V R K K P I F K K A T V T

FIG. 11b

E68 (conti'.) LEDHLACKCETVAAAARPVTM

E67 (conti'.) LEDHLACKCETVAAAARPVTM

E71 (conti'.) LEDHLACKCETVAAAARPVTM

E75 (conti'.) LEDHLACKCETVAAAARPVTM

FIG. 11C

TRANSFECTED E. COLI (WITH INCLUSION BODIES)

1) $T_{25}$ $E_{10}$ pH 8 & LYSOZYME/SONICATION
2) $T_{25}$ $E_{10}$ pH 8 & 1% TRITON $T_{2.5}$ $E_1$ pH 8
3) $T_{2.5}$ $E_1$ pH 8
4) 8 M UREA $T_{2.5}$ E, pH 8 & 10 mM DTT

↓

FUSION PROTEIN

1) ION EXCHANGE CHROMATOGRAPHY
2) DIALYSIS/LYOPHYLIZATION

↓

PURIFIED FUSION PROTEIN

1) CNBr DIGESTION
2) GEL FILTRATION
3) LYOPHILIZATION

↓

FUSION PROTEIN, MONOMERS & LEADERS

1) CM CELLULOSE CHROMATOGRAPHY
2) HPLC
3) LYOPHILIZATION

↓

MONOMERS

GLUTATHIONE-ASSISTED RESHUFFLING

↓

MONOMERS & DIMERS

HEPARIN-SEPHAROSE CHROMATOGRAPHY

↓

DIMERS
(ACTIVE)

FIG. 12

PRODUCTION OF PLATELET DERIVED GROWTH FACTOR (PDGF) AN MUTEINS THEREOF

This application is a divisional of Ser. No. 07/155,066 filed Feb. 11, 1988, now abandoned.

BACKGROUND OF THE INVENTION

This invention relates to the production and purification of synthetic polypeptides using recombinant DNA technologies, and to the modification of such polypeptides to forms which are biologically active. More particularly, this invention relates to methodologies which have been developed to produce human platelet-derived growth factor (PDGF) in prokaryotes, and to modify and change the conformation of the PDGF so produced into biologically active forms.

Human platelet-derived growth factor (PDGF) is a peptide hormone produced by human blood platelets which influences the regulation of a broad array of biological systems including wound repair, atherosclerosis, neoplasia, embroyogensis and bone marrow fibrosis. In wound repair, PDGF elicits both chemotaxic and mitogenic responses in fibroblasts, smooth muscle, and glial cells. Injury to endothelial linings is believed to cause platelets to adhere to exposed connective tissue at the wound site, and there to release PDGF. The released PDGF is thought to chemotaxically recruit fibroblasts, monocytes, glia, and smooth muscle cells to migrate to the site of the wound. PDGF is also believed to stimulate DNA synthesis in these cells, thereby increasing their proliferation rate. This mitogenic ability has made PDGF a valuable component of tissue culture media.

Native PDGF is a dimeric molecule consisting of two polypeptide chains, one or more of which may be glycosylated. The two chains (referred to as A or alpha and B or beta) are homologous but not identical. They have molecular weights of about 17,000 to 18,000 daltons and about 13,000 to 14,000 daltons, respectively. In vivo, the A and B chains are synthesized from larger precursors which are subsequently processed at the amino and carboxyl termini. The mature human A chain consists of 110 or 125 amino acids and various N-linked sugar side chains, the length and amino acid sequence being dependent on the tissue source. The fully processed human B chain is encoded by the C-sis gene and consists of 112 amino acids. It has been found to have a high degree of homology with the p28$^{sis}$ protein product of the v-sis transforming gene of simian sarcoma virus (SSV) (Johnsson et al., (1984) Embo. 3:921).

Biologically active PDGF can exist as an AA or BB dimer, having a molecular weight of about 35,000 daltons or about 32,000 daltons, respectively. There is also speculation that PDGF may exist as an AB heterodimer. At the present time there is no consensus as to whether the different forms of PDGF reflect different functional states. Monomers do not appear to exhibit any mitogenic activity.

The human PDGF dimer is glycosylated and processed into a biologically active, three-dimensional conformation. This conformation is maintained by relatively weak noncovalent hydrogen bonds, hydrophobic and charge interactions, and strong covalent bonds between sulfur atoms. The PDGF dimer has 8 such disulfide linkages which may be both inter- and intrachain bonds. Reduction of either the AA or BB dimer into its component monomeric chains destroys all biological activity.

Presently, several methods are known by which PDGF can be extracted from human platelets (Heldin et al., (1979) Proc. Natl. Acad. Sci. U.S.A. 76:3722–3726; Antoniades et al., (1979) Proc. Natl. Acad. Sci. U.S.A. 76:1809–1813). However, in addition to being expensive to perform, these methods are generally inefficient, yielding only up to about 5% of the original starting material. Improved recoveries have been obtained by following the procedure of Antoniades (U.S. Pat. No. 4,479,896) and Lipton et al. (U.S. Pat. No. 4,350,687), but yields are still limited by the availability of human platelets, the starting material. Furthermore, the therapeutic use of products derived from human blood carries the risk of transmission of a number of diseases such as Acquired Immune Deficiency Syndrome.

More recently, these problems have been circumvented by the expression of PDGF in genetically engineered eucaryotic cells such as yeast (EP Publication No. 0177957). Eucaryotes have the ability to modify a protein posttranslationally in a variety of ways. In the case of PDGF, such modification includes glycosylation, cleavage of leader sequences, folding, and formation of the intramolecular disulfide bonds requisite for biological activity.

Prokaryotes have been used to express many protein products of DNA recombinant technology despite their inability to posttranslationally modify and process many eucaryotic proteins. Their growth rate, and hence their rate of protein expression are faster than those of eucaryotes, in addition to being easy to manipulate and inexpensive to culture. Procedures have been developed for the in vitro renaturation of biologically active eucaryotic proteins (WO 86/05809). However, the success of the in vitro procedure has been limited severely by the complexity of the protein involved. For example, attempts to specifically reconstitute activity of A and B monomers by reoxidation of the reduced polypeptides have thus far failed (Raines and Ross (1982) J. Biol. Chem. 257:5154). Thus, what is needed is an improved method of producing commercially useful quantities of biologically active, genetically engineered complex eucaroyotic proteins.

Accordingly, it is an object of the present invention to provide a procedure for the production of biologically active PDGF in prokaryotic cells. Another object is to provide a method for obtaining biologically active recombinant PDGF in improved yields. Yet another object is to provide a facile method of producing biologically active PDGF which is efficient and inexpensive to perform.

A further object is to provide a recombinantly-produced polypeptide with substantially the same biological activity as PDGF. Yet a further object is to provide a formulation containing a recombinantly produced polypeptide having PDGF-like biological activity for therapeutic applications.

These and other objects of the invention will be apparent from the description, drawing, and claims that follow.

SUMMARY OF THE INVENTION

Briefly, this invention is directed to geneticially engineered PDGF polypeptides, DNA encoding these polypeptides, and methods of their production.

It has now been discovered that conformationally complex, biologically active PDGF species can be produced in prokaryotic cells. To the knowledge of the inventors, the prior art fails to suggest that such complex proteins can be made without recourse to the posttranslational biochemical machinery of eukaryotes.

More particularly, this invention provides PDGF polypeptides and analogs thereof (hereinafter collectively referred to as PDGF) which have been produced in prokaryotes such that they are free of native glycosylation, but which have biological activity similar to native, glycosylated PDGF. In addition, the invention provides novel recombinant DNAs encoding such polypeptides, and procedures for the expression and in vitro modification of the polypeptides so produced to biologically active forms. By practicing the method of the present invention, high yields of biologically active PDGF can be obtained inexpensively and efficiently through expression in prokaryotic cells, providing an improved, more cost effective production method.

In accordance with the invention, there is provided a renatured polypeptide produced in a prokaryotic host, such as *Escherichia coli* (*E. coli*), transformed with a recombinant DNA encoding that polypeptide, and free of native glycosylation. This polypeptide has an amino acid sequence sufficiently duplicative of that of PDGF such that when the polypeptide is oxidized in the presence of a chain of PDGF to form a dimer, the dimer is capable of inducing mitogenic activity in fibroblasts and chemotactic activity in smooth muscle cells.

The polypeptide may have an amino acid sequence which is substantially homologous with that of an A chain of a PDGF or an analog thereof. Such polypeptides can form either a heterodimeric or homodimeric PDGF species upon oxidation with a B chain or A chain, respectively, both of which have biological activity. Alternatively, the polypeptide may have an amino acid sequence which is substantially homologous with that of a B chain of PDGF or an analog thereof. This type of polypeptide also forms a heterodimeric or homodimeric PDGF species upon oxidation with an A chain or B chain, respectively, both of which have biological activity. The amino acid sequence of the PDGF polypeptide also can be truncated, can be that of the $Ser_1 \rightarrow Ala_1$ and/or the $Met_{12} \rightarrow Val_{12}$ muteins of the B chain, or can be another analog of a native A or B PDGF chain. Also, the A chain may take the endothelial or longer glioma form.

The invention also provides a DNA which includes a first nucleotide sequence containing a promoter/operator region operable in a prokaryote such as *E. coli*. The DNA includes a second nucleotide sequence operably linked to and under the direction of the promoter/operator region of the first nucleotide sequence. The second nucleotide sequence encodes a first polypeptide having an amino acid sequence sufficiently duplicative of a chain of a PDGF to enable it to have the biological activity of PDGF when oxidized in the presence of a second PDGF chain. This first polypeptide may be substantially homologous with an A or B chain of a PDGF. Alternatively, this first polypeptide may consist of a $Ser_1 \rightarrow Ala_1$ and/or a $Met_{12} \rightarrow Val_{12}$ mutein of a B chain of a PDGF, a truncated A or B chain, or other activatable analog of an A or B chain.

The DNA of the invention may further contain a third nucleotide sequence interposed between the first and second encoding a leader peptide. This third sequence is operably linked to, and under the direction of the promoter/operator region such that it and the second nucleotide sequence are expressable as a fused polypeptide. A codon specifying a Met residue, which links the C-terminus of the third polypeptide to the N-terminus of the second polypeptide, and which is cleavable by cyanogen bromide, may be included in the third nucleotide sequence.

In accordance with the invention, the method includes (1) expressing in a prokaryote a DNA sequence which encodes a fused peptide containing a leader and a PDGF or PDGF-like chain which ultimately will have the biological activity of PDGF. Its expression is under the direction of a promoter/operator region operably linked to nucleotide sequences encoding the fused peptide; (2) cleaving the fused peptide to release the PDGF polypeptide; (3) combining the PDGF polypeptide with a second PDGF chain in vitro; and (4) modifying the first and second polypeptides in vitro so as to produce a dimer of PDGF which has biological activity. In accordance with the invention, the recombinant DNA molecules may be derived or synthesized by techiques generally known to those skilled in the art, and as disclosed herein.

The PDGF polypeptides produced by the method of the invention may be homologous with the glioma species of an A chain of PDGF. In this case, to produce a heterodimer, the glioma-type A chain is present in excess during the combining and modifying steps, resulting in the production of a biologically active PDGF heterodimer. Alternatively, if the PDGF polypeptide chain is homologous with the endothelial species of an A chain of PDGF, and the B chain is present in excess during the combining and modifying steps, the result is the production of a biologically active PDGF heterodimer.

The second polypeptide which is combined in vitro with the first to produce an active species may itself be produced by conducting the expressing, recovering, and cleaving steps of the method described above, or may be derived from other sources.

The modifying step includes contacting the first and second polypeptides with a physiologically compatible substance that facilitates disulfide bond formation between sulfhydryl group-containing amino acid residues of the polypeptides. Such treatment results in a change in the conformation of the polypeptides such that they become a dimeric molecule having the biologically activity of PDGF. An exemplary substance, according to the method of the invention, is glutathione, present in the solution in both reduced and oxidized forms. In a preferred embodiment, the contacting step is performed with a solution containing a mixture of oxidized and reduced glutathione, and at a pH in the range of about 7.0 to about 8.0. The oxidized and reduced species of glutathione being present at a ratio of about 1:10, the former being present at a concentration of about 0.1 mM, and the later at about 1.0 mM.

BRIEF DESCRIPTION OF THE DRAWING

The foregoing and other objects of this invention, the various features thereof, as well as the invention itself, may be more fully understood from the following description, when read together with the accompanying drawings in which:

FIG. 1 is a representation of a synthetic recombinant DNA of the invention containing a vector-derived polylinker region and a structural gene encoding a glioma A chain of PDGF, and includes a restriction map, and the corresponding amino acid sequence;

FIG. 2 is a representation of a synthetic recombinant DNA of the invention containing a structural gene encoding an endothelial A chain of PDGF, a restriction map, and the corresponding amino acid sequence;

FIG. 3 is a schematic representation of DNA of the invention containing a vector-derived polylinker region and encoding a (C-sis) B chain of PDGF, a restriction map, and the corresponding amino acid sequence;

FIGS. 4–7 are representations of a recombinant DNAs of the invention containing structural genes encoding exemplary B chain muteins, restriction maps, and corresponding amino acid sequences;

FIG. 8 is a representation of a recombinant DNA showing a Trp operator/promoter region, a structural gene encoding the modified LE leader peptide, and the corresponding amino acid sequence for the LE peptide. This operator/promoter—leader DNA is preferred for expressing the PDGF A and B chains of FIGS. 1–7 in E. coli.

FIG. 10 discloses a comparison of the amino acid sequences of endothelial and glioma A chains;

FIG. 12 is a diagramatic summary of an exemplary method for the production of biologically active PDGF;

DESCRIPTION OF THE INVENTION

Figure 9:
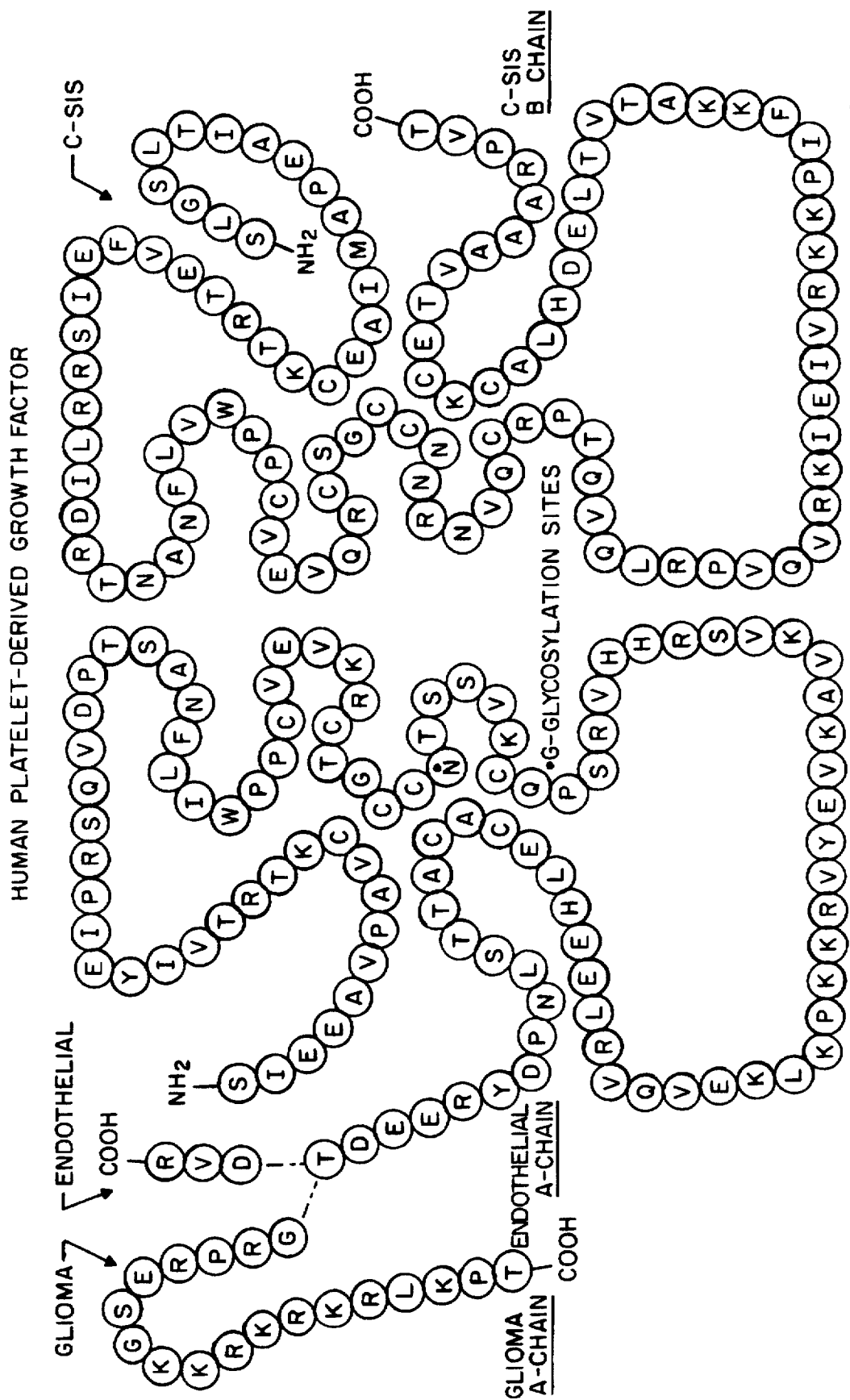
FIG. 9 is a diagramatic, two-dimensional representation of native amino acid sequences of the A and B chains of PDGF derived from different tissue sources.

PDGF has the ability to induce mitogenic and chemotactic responses in cells involved in the wound healing process, and therefore is of potentially great therapeutic value. However, the availability of commercial quantities of this polypeptide has been limited by the small amounts able to be isolated from human tissue in active form or produced in active form by recombinant eucaryotic hosts. Therefore, prokaryotic cells capable of faster, more efficient, and larger volume translation were induced to express PDGF chains.

To become biologically active, a PDGF chain or most any polypeptide must assume a specific tertiary conformation. The precise conformation is determined and maintained by a combination of covalent, ionic, hydrogen bonding, van der waals, and other interactions of the individual amino acid residues.

Among the strongest interactions responsible for tertiary conformation of a protein is the covalent interaction of one sulfhydryl group with another, forming a disulfide linkage upon oxidation. Hypothetically, any two sulfhydryl group-containing amino acid residues of a polypeptide could form a disulfide linkage, resulting in a multiplicity of possible combinations of disulfide linkages and resulting tertiary conformations. Realistically, however, steric hindrances discourage many combinations as they result in inactive, thermodynamically unstable molecules.

Eucaryotes can form disulfide linkages between appropriate amino acid residues of newly synthesized complex proteins, but prokaryotes are not known to have this ability to form the proper disulfide linkages in these eucaryotic proteins because of different translational and posttranslational machinery. Therefore, prokaryotically-produced recombinant eucaryotic proteins which require disulfide bonding for activity must be modified by in vitro methods. This is accomplished in accordance with the invention by exposing the purified translational product to a physiologically compatible substance which has the ability to perform or initiate the necessary oxidation between reduced sulfhydryl groups. The substance may itself have oxidized and reduced disulfide bonds, the presence of which changes the state of the disulfide linkages in PDGF until they reach an equilibrum, resulting in the most stable conformation of the dimer. A preferable substance is glutathione, present in solution in both oxidized and reduced forms. Other useful substances include dithiothreitol, beta-mercaptoethanol, and thioredoxin. Alternatively, this substance may be an enzyme such as disulfide isomerase which has the ability to create disulfide linkages.

In any event, the greater the number of possible binding combinations, the more difficult it becomes to perform the correct linkages in vitro. The PDGF dimer has 8 disulfide bonds and 2,027,025 theoretically possible inter- and intra-chain combinations of sulfhydryl group-containing amino acids which could bind. The combination or combinations of disulfide linkages which result in a biologically active molecule is unknown. Therefore, it was unexpected that a prokaryotically-produced, genetically engineered PDGF dimer could assume a tertiary conformation having biological activity by being oxidized and disulfide bonded in vitro.

It also could not have been anticipated that unglycosylated forms of PDGF (i.e., AA, AB), produced according to the method of the present invention, would have significant biological activity, similar in some cases to the activity of native PDGF or eucaryotically-produced, synthetic PDGF which are glycosylated. The invention is based on the discovery that commercially feasible quantities of biologically active PDGF can be obtained efficiently and inexpensively by expression in prokaryotes and subsequent in vitro modificatiaon.

The practice of this invention can be divided into two phases. The first phase consists of the design, synthesis, and expression of recombinant DNAs encoding the A and B chains of PDGF and related muteins in a prokaryotic host. The second phase relates to the purification and in vitro processing of the encoded PDGF polypeptides into biologically active forms.

Phase 1: Expression of Recombinant PDGF Genes

The processes for designing, manipulating, and recombining DNA which encode PDGF chains or any amino acid sequences of interest are generally well known in the art, and therefore, are not described in detail herein. Methods of identifying and isolating genes encoding proteins of interest, or for constructing such genes, are well understood and developed. These processes are described in the patent and other literature (e.g., U.S. Pat. No. 4,431,739; Maniatis et al., A Cloning Manual, Cold Spring Harbor, 1984 et seq.). In general, the methods involve selecting genetic material encoding amino acids which define the polypeptide of interest according to the genetic code.

Accordingly, the construction of DNAs encoding various A and B chains of PDGF disclosed herein and shown in FIGS. 1 through 7, or other analogs devised by those skilled in the art, can be performed using known techniques. These techniques may involve the use of various restriction enzymes which make sequence specific cuts in DNA, DNA ligases which join deoxyribonucleic acid sequences, polymerases which catalyze the formation of new genetic material, probes for isolating PDGF-encoding sequences, and enzymatic addition of sticky ends to blunt-ended DNA.

One method for obtaining DNA encoding the A and B chains of PDGF disclosed herein is by assembly of synthetic oligonucleotides produced in a conventional, automated, polynucleotide synthesizer, followed by ligation with appropriate enzymes, and conventional amplification. For example, overlapping, complementary DNA fragments comprising 15 bases may be synthesized semi-manually using phosphoramidite chemistry, with end segments left unphosphorylated to prevent polymerization during ligation. One end of the synthetic DNA is left with a "sticky end" corresponding to the site of action of a particular restriction endonuclease, and the other end is left with an end corresponding to the site of action of another restriction endonuclease. Alternatively, this approach can be fully automated. The DNA encoding the A and B chains may be created by synthesizing longer single strand fragments (e.g., 50–100 nucleotides) in, for example, a Biosearch oligonucleotide synthesizer, and then ligating the fragments.

Alternatively, DNA encoding the protein of interest may be synthesized as cDNA from MRNA specific for that protein.

The DNA is composed of two or three distinct linked nucleotide sequences. The first sequence is a promoter/operator region operable in a prokaryote. Such a sequence is the Trp promoter/operator depicted in FIG. 8. Other promoter/operator regions operable in prokaryotes will be useful as well. Linked to this DNA is a second sequence encoding an A or B chain PDGF polypeptide, the protein of interest, which ultimately will be harvested.

Figures 11, 11A:
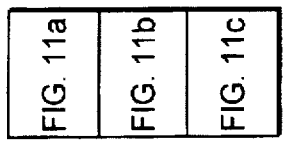
FIG. 11 discloses a comparison of the native (E-68) amino acid sequence and of various B chain muteins.

The second nucleotide sequence of the synthetic DNA may encode any species of A or B chain, or analogs thereof. Exemplary and currently preferred nucleic acid and amino acid sequences are illustrated in FIGS. 1–7. There are at least two known human forms of the A chain, depicted schematically in FIGS. 9 and 10; one is derived from glioma cells, and a second shorter species is derived from endothelial cells. The native B chain has been found to be homologous with the SSV v-sis gene product, and thus the second nucleotide sequence may encode a viral protein as well. Alternatively, the second nucleotide sequence may encode a mutein of an A or B chain obtained by changing one or several amino acids of the sequence, or truncating an A or B chain to produce an analog. Any number of changes in the nucleotides encoding the amino acid sequence of a particular chain may be changed as long as a dimer of the resulting mutein still possesses biological activity characteristic of PDGF. Representative examples include the $Ser_1$-$Val_{12}$, $Ser_1$-$Met_{12}$, $Ala_1$-$Met_{12}$, and $Ala_1$-$Val_{12}$ muteins of a B chain, the amino acid sequences of which are compared in FIG. 11. The PDGF activity of other muteins and analogs can be known with certainty only after such materials have been produced. However, experience with a given biologically active protein derived from different species indicates that significant changes in amino acid sequences can be made while retaining biological activity. The methods disclosed herein can be used to produce all such species of PDGF.

The optional third sequence encodes a leader polypeptide. It is interposed between the first and second sequences, and is operably linked to the first sequence such that the second and third sequences are expressable as a fused polypeptide. Depicted in FIG. 8 is a representative leader peptide, the modified LE peptide, which was designed to enhance expression in *E. coli*. Of course, other leaders may be used, and may be required if a different procaryotic cell type is used as an expression vehicle. The third sequence may further encode a Met residue at its C-terminal end which serves to link the leader peptide to the N-terminus of an A or B chain, and which provides a conveniently located cyanogen bromide cleavage site. In FIG. 8 this Met residue is coded for by nucleotides at positions 260–262.

The expression of these synthetic PDGF-encoding DNA molecules is achieved via the transformation of a prokaryotic host cell with a vector containing that DNA. Various types of prokaryotic host cells are known and available, *E. coli* being the most preferred. Other prokaryotes that may be used include Bacillus. Conventional transfection techniques are also known to those skilled in the art, and are useful in the practice of this invention.

Various types of vectors may be used in the transfection such as plasmids and viruses including bacteriophages. These vectors contain various promoter/operator sequences and other regulatory DNA sequences which are known and available, and which are used in achieving expression. The vectors may exploit various marker genes which impart to a successfully transfected cell a detectable phenotypic property that can be used to identify which of the family of clones has successfully incorporated the recombinant DNA of the vector.

Phase 2: Processing of the Expressed PDGF Polypentides

The production of the various PDGF chains has heretofore been achieved by expression in eucaryotes which are capable of posttranslational cleavage, disulfide bond formation, and glycosylation, thereby yielding a biologically active PDGF molecule. It has been determined and is herein disclosed that various PDGF chains expressed in a prokaryote may be cleaved, combined, and disulfide bonded in vitro to yield PDGF molecules which are also biologically active despite being unglycosylated. In fact, the activity of some species of this bacterially produced, unglycosylated AB or AA PDGF rivals that of platelet-derived PDGF. See FIG. 18, comparing chemotactic activity of native PDGF derived from platelets and a recombinant B—B dimer (circles, $Ala_1 \rightarrow Val_1$ mutein). The chemotactic activity of the homodimeric and heterodimeric PDGF species was determined according to Martinet et al. (N. Eng. J. Med (1987) 317: 202.), and mitogenic activity by the established method of Antoniades et al. (Proc. Natl. Acad. Sci. USA (1979) 76:1809). The biological activities of various PDGF hetero- and homodimers constructed from different forms of the A and/or B chains are compared in FIGS. 13–18. Although all dimeric forms have at least some activity, the AA homodimers appear to have the least mitogenic and chemotactic activities.

According to the method of the invention, and as summarized in FIG. 12, biosynthetic, biologically active, oxidized PDGF dimers can be produced. Variations in the purification protocol shown in TABLE I and discussed in more detail below may selectively yield a particular species of dimer. Briefly, a prokaryotic host is transformed with a vector containing DNA encoding a PDGF chain and a leader peptide linked thereto, the leader peptide enabling the prokaryotic host to express and to retain intracellularly the eucaryotic translation product as a fusion protein. The fusion protein is translated from the transfected DNA and stored within the host cell. In *E. coli*, storage is accomplished as the protein aggregates as inclusion bodies.

To obtain the PDGF chains from the fusion protein, the inclusion bodies are purified from harvested host cells using any known purification method. Such methods may include, for example, enzymatic and detergent lysis of the host cells. The fusion protein is then cleaved to remove the extraneous leader peptide portion of the molecule. Preferably, removal of the leader peptide is accomplished by cleavage with cyanogen bromide (CNBr) at a Met residue linking the leader peptide to the A or B chain. Of course, as those skilled in the art will appreciate, many other cleavage sites may be incorporated 5' of the N terminus of the PDGF chain and subsequently cleaved using site specific chemical cleavage or a suitable endoprotease. The released PDGF chain or monomer can then be isolated by known procedures such as gel filtration, CM cellulose chromatography, or high pressure liquid chromatography (HPLC).

TABLE I

| PDGF Species-Procedure | $BB_{c-sis}$ | $BB_{Ala_1-val_{12}}$ |
|---|---|---|
| Ion Exchange Chrom. | CM Cellulose 6M urea $A_{2.5}$ $E_1$ pH 6 + 10 mM DTT 0–0.3M NaCl | CM Cellulose 6M urea $A_{2.5}$ $E_1$ pH 6 + 10 mM DTT 0–0.3M NaCl |
| CNBr Digest | 10 mg/ml 5% formic 100× CNBr 16 hr RT | 10 mg/ml 70% formic 1000× CNBr 16 hr RT |
| Gel Filtration | GF-05 1.0% acetic acid | GF-05 1.0% acetic acid |
| CM Cellulose | 6M urea $A_{2.5}$ $E_1$ pH 6 + 10 mM DTT 0–0.2M NaCl | 6M urea $A_{2.5}$ $E_1$ pH 6 + 10 mM DTT 0–0.2M NaCl |
| HPLC | pH 2 0.1% TFA 30–55% $CH_3CN$ | pH 2 0.1% TFA 30–55% $CH_3CN$ |
| Reshuffling | 0.5 mg/ml 0.5M urea pH 8 1 mM GSH 0.1 mM GSSG | 0.5 mg/ml 0.5M urea pH 8 1 mM GSH 0.1 mM GSSG |
| Heparin-Sepharose | pH 7 0.1–1N ammonium acetate | pH 7 0.1–1N ammonium acetate |

| PDGF Species-Procedures | $BB_{trunc}$ | $AA_{endo}$ |
|---|---|---|
| Ion Exchange Chrom. | CM Cellulose 6M urea $A_{2.5}$ $E_1$ pH 6 + 10 mM DTT 0–0.3M NaCl | CM Cellulose 6M urea $A_{2.5}$ $E_1$ pH 6 + 10 mM DTT 0–0.3M NaCl |
| CNBr Digest | byproduct of B(c-sis) cleavage | 10 mg/ml 70% formic a. 1000× CNBr 16 hr RT |
| Gel Filtration | GF-05 1% acetic acid | GF-05 1% acetic acid |
| CM Cellulose | 6M urea $A_{2.5}$ $E_1$ pH 6 + 10 mM DTT 0–0.2M NaCl | 6M urea $A_{2.5}$ $E_1$ pH 6 + 10 mM DTT 0–0.2M NaCl |
| HPLC | pH 2 0.1% TFA 30–55% $CH_3CN$ | pH 2, 0.1% TFA 25–55% $CH_3CN$ |
| Reshuffling | 0.5 mg/ml 0.5M urea pH 8 1 mM GSH 0.1 mM GSSG | 0.5 mg/ml 0.5M urea pH 8 1 mM GSH 0.1 mM GSSG |
| Heparin-Sepharose | pH 7 0.1–1N ammonium acetate | pH 7 0.1–2N ammonium acetate |

| PDGF Species-Procedures | $AA_{glio}$ | $A_{glio}/B_{trunc}$ |
|---|---|---|
| Ion Exchange Chrom. | DEAE cellulose 6M urea $T_{2.5}$ $E_1$ pH 8 + 10 mM DTT 0–0.3M NaCl | — |
| CNBr Digest | 10 mg/ml 40% formic a. 1000× CNBr 16 hr 37° C. | — |
| Gel Filtration | GF-05 1% acetic acid | — |
| CM Cellulose | 6M urea $A_{2.5}$ $E_1$ pH 6 + 10 mM DTT 0–0.2M NaCl | — |
| HPLC | pH 2, 0.1% TFA 25–55% $CH_3CN$ | — |
| Reshuffling | 0.5 mg/ml 0.5M urea pH 8 1 mM GSH 0.1 mM GSSG | 0.5 mg/ml 2A:1B 0.5M urea pH 8 1 mM GSH 0.1 mM GSSG |
| Heparin-Sepharose | pH 7 0.1–2N ammonium acetate | pH 7 0.1–2N ammonium acetate |

TABLE I-continued

| Procedures | $A_{endo}/B_{c-sis}$ |
|---|---|
| Reshuffling | 0.5 mg/ml 1A:2B 0.5M urea pH 8 1 mM GSH 0.1 mM GSSG |
| Heparin-Sepharose | pH 7 0.1–1N ammonium acetate |

$A_{2.5}$ means 2.5 mM ammonium acetate;
$E_1$ means 1 mM EDTA;
100× CNBr and 1000× CNBr means CNBr is present at 100-fold and 1000-fold excess The isolated monomer is then combined with a second PDGF monomer. The second monomer may be produced recombinantly as disclosed herein or may be derived from other sources. The monomers present together in solution are then subjected to conditions under which disulfide bonding (or oxidation) occurs between various sulfhydryl group-containing amino acids in the PDGF chains. It is not known whether interchain disulfide bonds are formed, although the dimers behave like a single, covalently bonded protein in a gel, and migrate as separate species after reduction. Any physiologically compatible substance which has oxidizing capabilities is useful for this purpose. Many such materials are known to those skilled in the art. These include mixtures of reduced and oxidized forms of, for example, glutathione, thioredoxin, dithiothreitol, beta-mercaptoethanol, and disulfide isomerase. The use of glutathione is preferable, and more particularly, oxidized (GSSG) and reduced (GSM) glutathione in a solution having a pH of about 7.0 to 8.0. It has been further determined that optimum in vitro oxidation of PDGF chains occurs when the oxidized and reduced glutathione species are present in the solution in a ratio of about 1:10, with the most preferable concentrations of such species being 0.1 mM and 1.0 mM, respectively. A dimeric AA, BB, or AB PDGF molecule having biological activity results from this "glutathione shuffle".

When A and B chains are present in reduced form in solution, a degree of control can be exercised over whether an AA, BB, or AB dimer is produced by setting the concentration of the reduced monomers at the outset. For example, when the endothelial form of the A monomer is used, an excess of B monomer results in preferential formation of the heterodimeric PDGF species. When the glioma form of the A monomer is used, an excess of A monomer results in preferential formation of heterodimer.

The following examples more fully illustrates preferred features of the invention, but are not intended to limit the invention in any way. All of the starting materials and reagents disclosed below are known to those skilled in the art, and are available commercially or can be prepared using well-known techniques.

A. Cloning of synthetic gene blocks in the PUC8 vector:

A gene unit encoding a PDGF chain produced either by reverse transcription of mRNA for PDGF, or by the enzymatic assembly of synthetic oligonucleotides is cloned into the pUC8 cloning vector, and plated with competent E. coli strain JM83 on LB agar containing 50 ug/ml Ampicillin at 50 ug/ml X-gal indicator dye substrate (Messing et al., Nucleic Acids Res. (1981) 9:309). The pUC8 plasmid without insert gives rise to blue colonies of JM83 cells, while pUC with gene insert produces white colonies. White colonies are picked into 5 ml LB broth culture medium containing 50 ug/ml Ampicillin, and incubated overnight in a rotary shaker incubator at 37 degrees Centigrade.

B. Analysis of clones by restriction digest:

Plasmid DNA is prepared from these cultures by the alkaline lysis procedure (Maniatis et al., Molecular Cloning, a Laboratory Manual (1982) Cold Spring Harbor Laboratory, pp 88–91). The DNA is analysed by restriction digestion with suitable enzymes, followed by polyacrylamide gel electrophoresis (PAGE).

C. DNA sequence analysis of cloned genes:

All synthetic genes are analyzed by dideoxy sequencing according to Sanger (J. Mol. Biol. (1975) 94:441). A given gene insert is isolated by restriction digestion followed by PAGE on 5% gels. After electroelution of the DNA fragment from the gel, the fragment is cloned into the ml3 RF (replicative form) vector, transformed into competent cells of the *E. coli* strain JM101, and plated in the presence of X-gal and IPTG. White plaques are picked, and the infected cells are grown up overnight in 2×yt broth. M13 recombinant phages are then isolated from culture supernatants by precipitation with polyethylene glycol. Single stranded phage DNA template for sequencing is prepared by phenol chloroform extraction.

Positive clones are thus selected and are retained for assembly with additional genes. DNA sequencing is performed on every assembly or modification step. DNAs encoding A and B chains produced in accordance with the foregoing methods are set forth in FIGS. 1–7 of the drawing. A summary of the procedure for producing the active PDGF dimers from the DNA is set forth in FIG. 12 and in more detail below.

D. Expression:

The gene is taken from the pUC cloning vector and inserted, along with a synthetic TRP promoter/operator and downstream PDGF structural gene, into an expression vector derived from pBR322. This expression vector is then transformed into competent *E. coli* hosts which express the fusion protein and store it in inclusion bodies.

E. Solubilization of inclusion bodies:

Cells are resuspended in 25 mM Tris, 10 mM EDTA, pH 8 (1 gram cells per 10 ml of buffer). Lysozyme is added to a final concentration of 0.1 mg/ml. The suspension is stirred for 30 min., sonicated, and centrifuged. The resulting pellet is resuspended in 25 mM Tris, 10 mM EDTA, pH 8 and 1% Triton X-100 (detergent), stirred for 1 hour, and centrifuged. The resulting pellet is then resuspended in 8 M urea, 2.5 mM Tris, 1 mM EDTA, 10 mM DTT, pH 8. The solution is stirred for 30 minutes, centrifuged, and the supernatant is retained.

The remaining steps of the production procedure involve purification of the fused proteins using ion exchange chromatography, cleavage with CNBr, purification of the PDGF chains using gel filtration, CM cellulose, and HPLC, forming two chain active species by oxidation, and purification of active materials on Heparin Sepharose. The currently preferred conditions for each of these steps for each of the various species produced in these examples is set forth in Table I above. Further particulars of the preferred protocol are set forth in steps F through K.

F. Ion exchange chromatography of the fusion protein:

A CM cellulose column (2.5 ml of resin per gram of cells) is equilibrated in 6 M urea, 2.5 mM ammonium acetate, 1 mM EDTA, 10 mM DTT, pH 6 (CM column buffer). The 8 M urea supernatant is adjusted to pH 6 and loaded onto the column. The loaded column is then washed in CM column buffer. Protein bound to the column is eluted with a gradient of 0–0.3 M NaCl in CM column buffer (333 ml per 10 ml resin). Column fractions are characterized on Laemlli 15% reducing-denaturing gels.

The fractions which contain the cleanest fusion protein are pooled, dialysed against water at pH 3, and lyophilized.

G. CNBr cleavage of the fusion protein into PDGF B chain monomers:

The fusion protein is resuspended in 5% formic acid at a particular concentration. CNBr is then added, and the solution is stirred at room temperature for 8–24 hours. TABLE II gives the optimum conditions for the production of various exemplary PDGF B chain constructs disclosed herein. After digestion the reaction solution is then subjected to gel filtration through GF-05 Trisacryl in 0.1N acetic acid. The effluent is then lyophilized.

TABLE II

| Fusion Protein | Protein (mg/ml) | Formic Acid Conc. | CNBr Excess | Time (Hrs) | PDGF Monomers |
|---|---|---|---|---|---|
| $Ala_1$-$Val_{12}$ | 8 | 70 | 1000× | 16 | $Ala_1$-$Val_{12}$ |
| $Ala_1$-$Met_{12}$ | 2 | 10 | 100× | 16 | $Ala_1$-$Met_{12}$ |
| $Ser_1$-$Val_{12}$ | 8 | 70 | 1000× | 16 | $Ser_1$-$Val_{12}$ |
| $Ser_1$-$Met_{12}$ | 2 | 5 | 100× | 16 | $Ser_1$-$Met_{12}$ |

H. CM cellulose purification of PDGF B chain monomers:

The digests were resuspended in 6M urea, 2.5 mM ammonium acetate, 1 mM EDTA, 10 mM DTT, pH 6. The protein concentration was 2 mg/ml. The CM column (3 ml of resin per 10 mg of digest) was equilibrated in CM column buffer. The digest was loaded onto the column, washed in CM column buffer, and eluted with a gradient of 0–0.3M NaCl in CM column buffer (333 ml per 10 ml resin). Fractions determined to contain the PDGF monomer are then pooled.

I. HPLC purification of monomers:

Monomers prepared in step H are loaded onto a $C_{18}$ column and eluted using an acetonitrile/TFA gradient (25–55% CH3CN over 90 min). Fractions are characterized on Laemmli 15% reducing—denaturing gels. PDGF-containing fractions are pooled, and the acetonitrile is removed by rotory evaporation. The monomers are then lyophilized.

J. Refolding of the monomers into PDGF dimers:

The lyophilized monomers are reconstituted in 2.0M urea at 2 mg/ml, and buffer is added to achieve a final concentration of 0.5M urea, 0.5 mg/ml protein, 50 mM Tris, pH 8, 1.0 mM reduced glutathione (GSH), and 0.1 mM oxidized glutathione (GSSG).

Refolding proceeds at room temperature for 16 hours. The resulting mixture is then dialyzed against 0.1N acetic acid. It should be noted at this point that the protein concentration can vary over a broad range (0.1 to 5 mg/ml) with very little impact on refolding. At the higher protein range there is some aggregation, but the yield of dimer appears to remain relatively constant.

K. Heparin sepharose purification of PDGF dimers The heparin Sepharose is equilibrated in 0.1N acetic acid, pH 7 (the pH is adjusted with amonium hydroxide). The refolded mixture is loaded onto the column at 1 mg protein per ml of resin, washed with the acetic acid buffer, and eluted with a gradient of 0.1–1.0N acetic acid, pH 7 (30 ml buffer per ml resin).

The clean, well-separated fractions are pooled, sterile filtered, and lyophilized or frozen. The material is then assayed for biological activity, and the refolded dimer is localized by characterizing fractions on 15% Laemlli non-reducing gels.

Figure 13A:
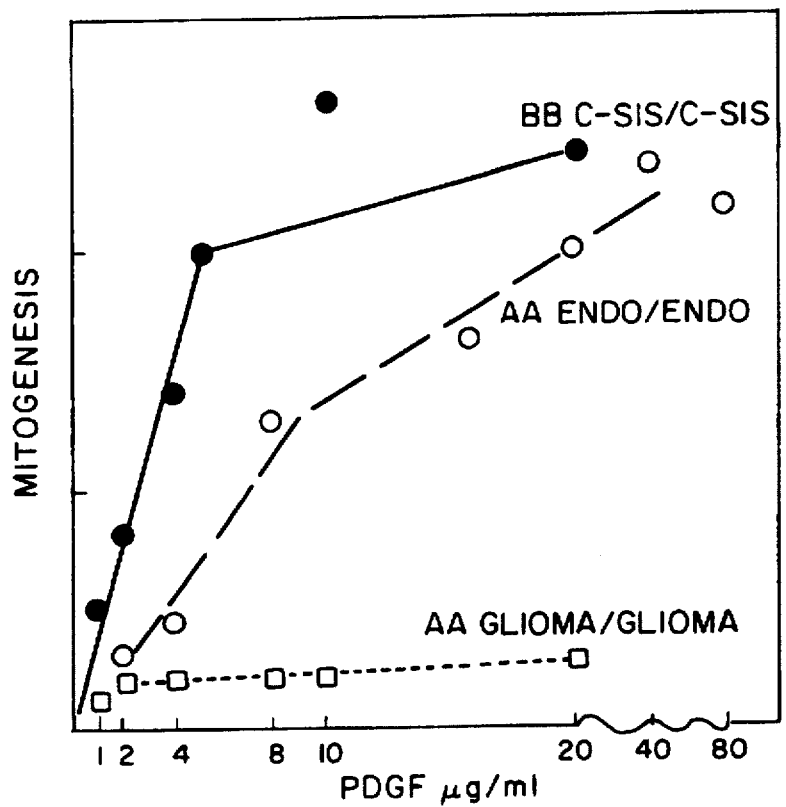
FIGS. 13–17 parts A and B of each are graphic comparisons of the mitogenic (A) and chemotactic (B) activities of various dimeric forms of PDGF produced in accordance with the invention.
Figure 13B:
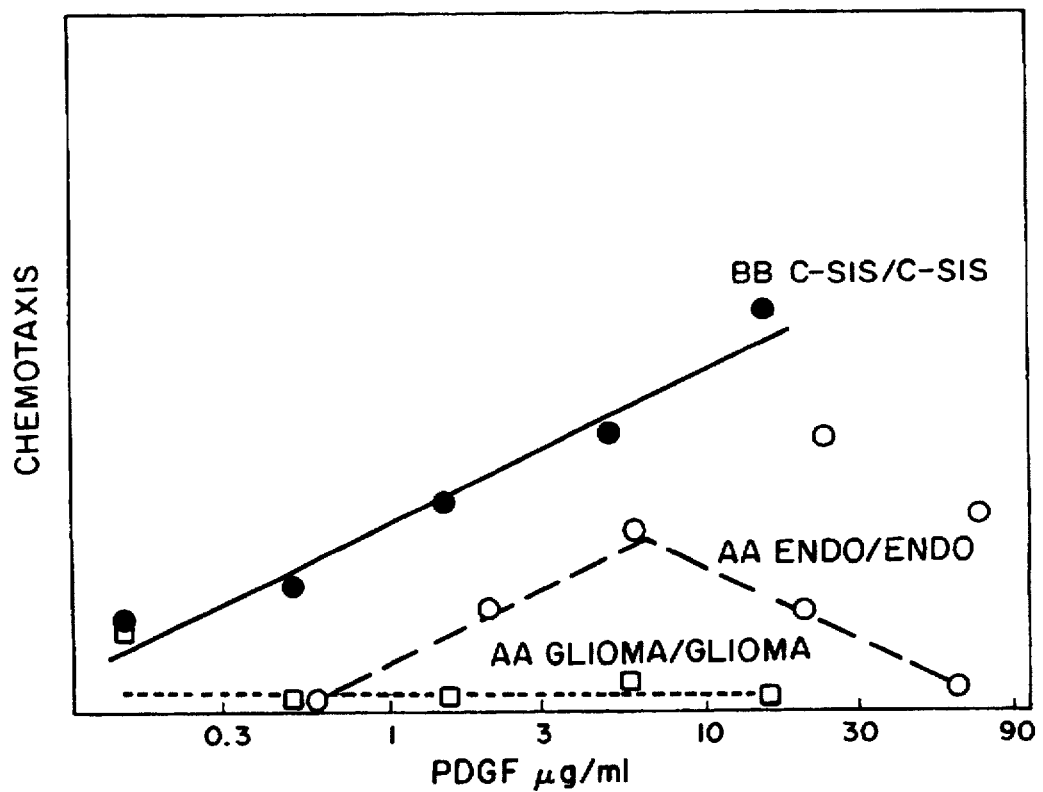
Figure 14A:
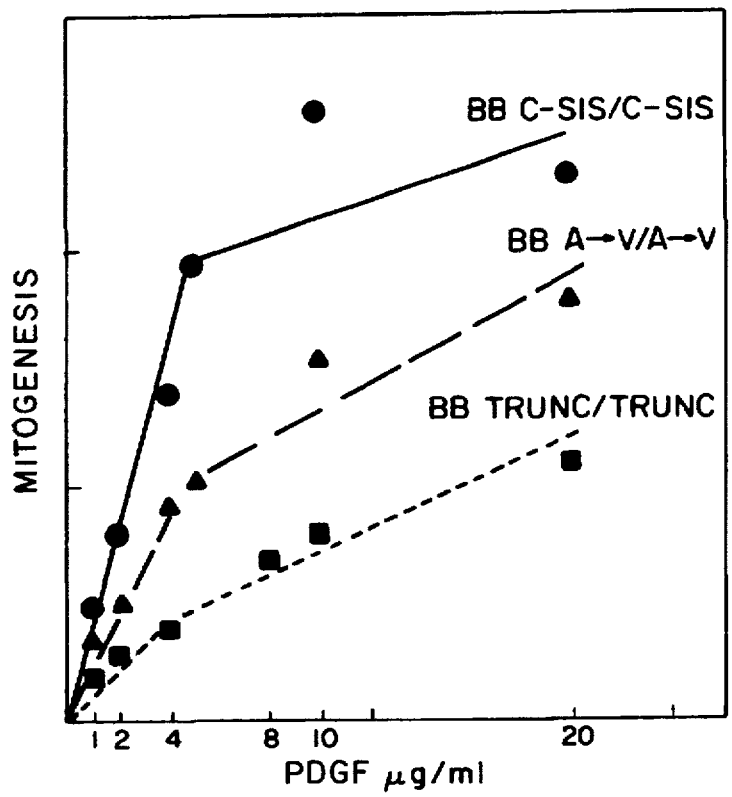
Figure 14B:
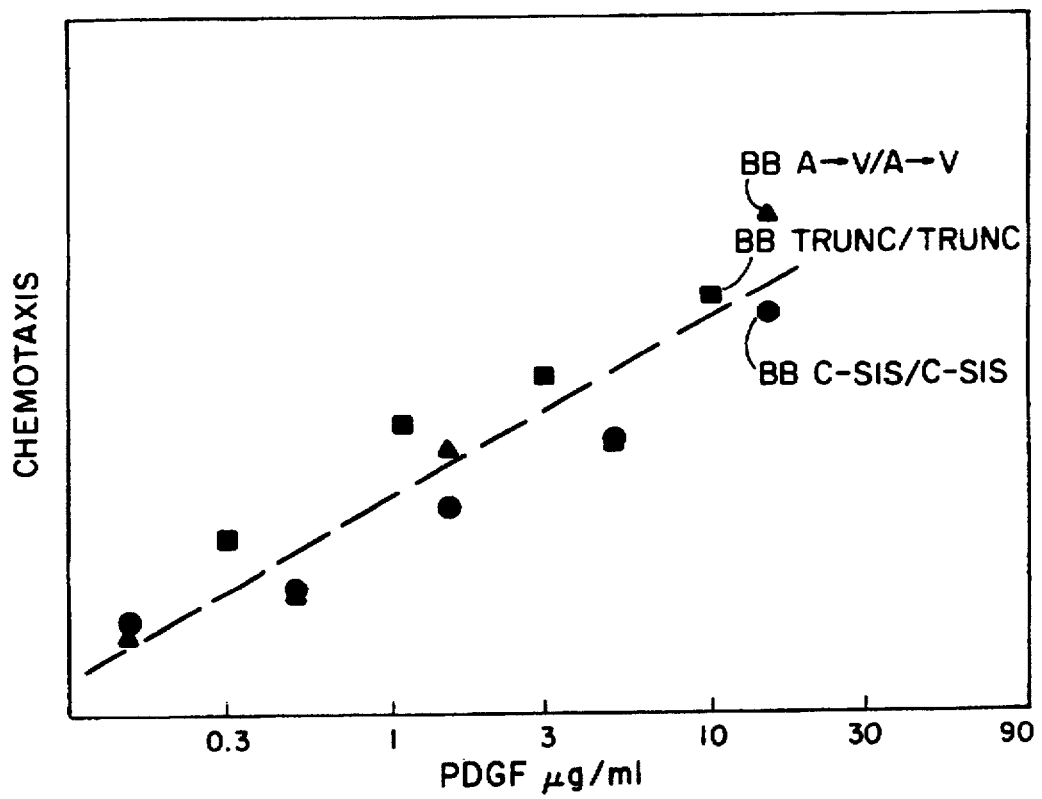
Figure 15A:
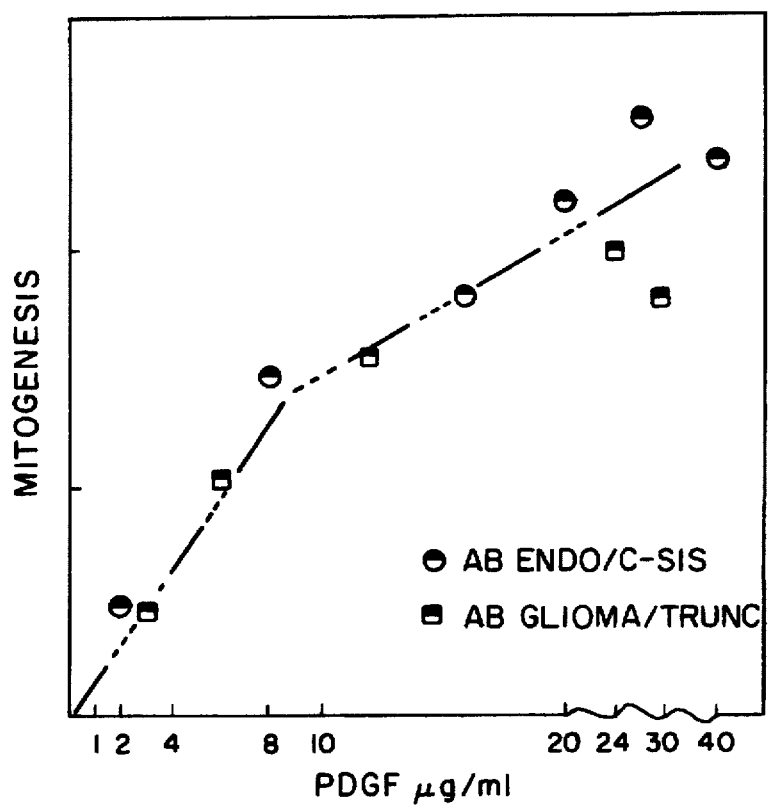
Figure 15B:
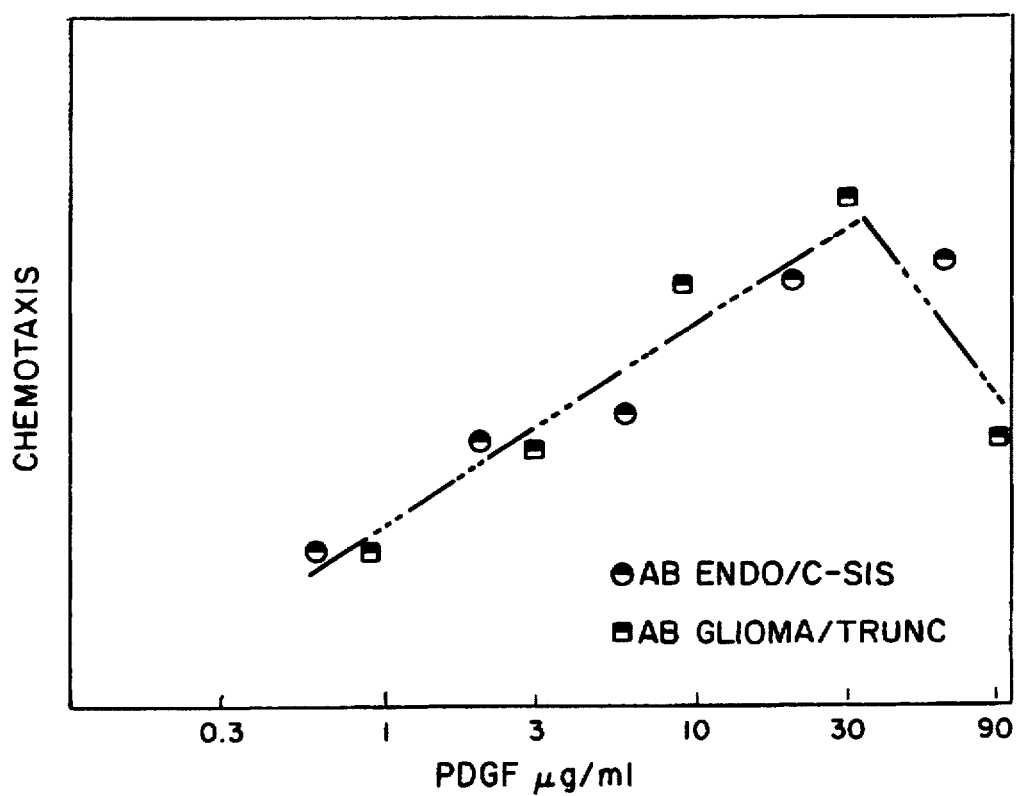
Figure 16A:
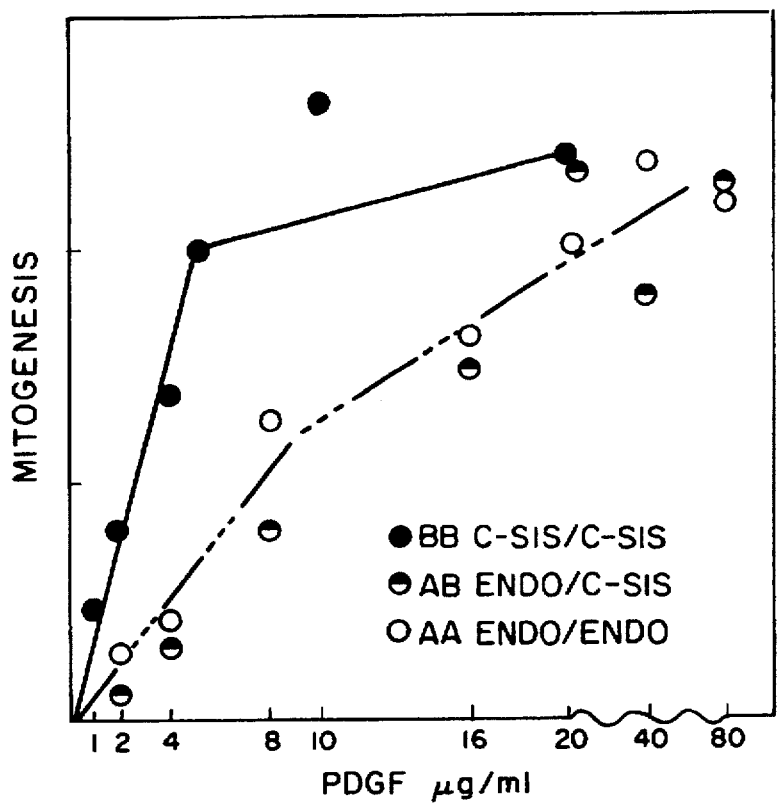
Figure 16B:
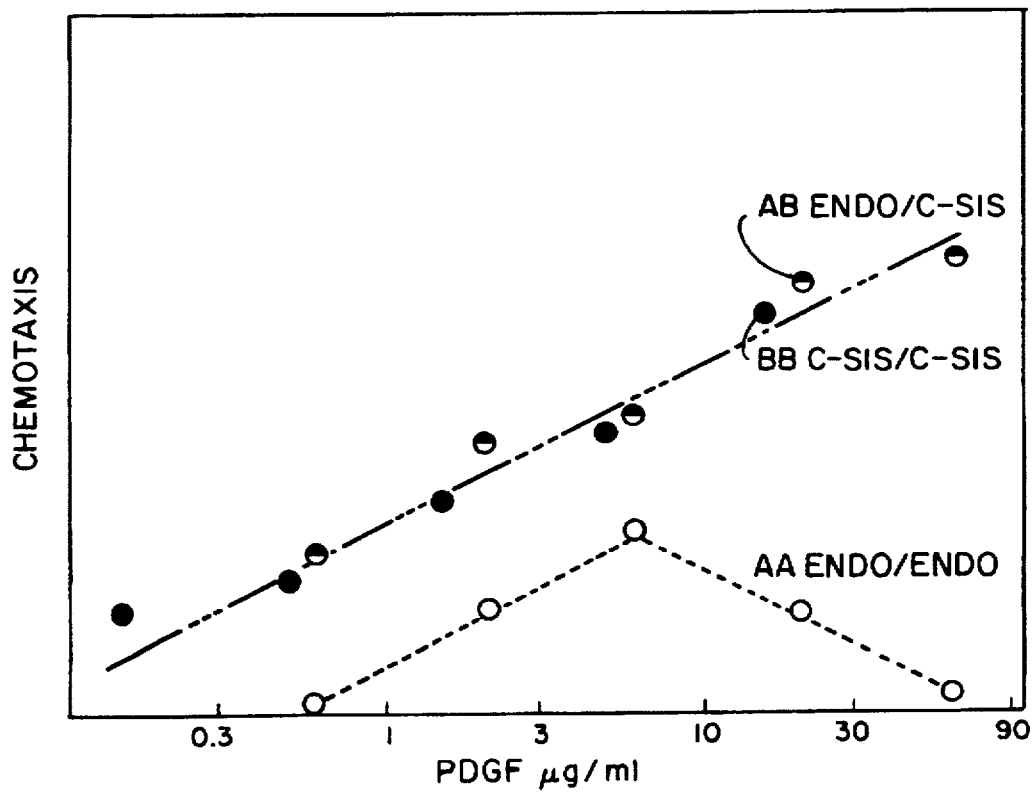
Figure 17A:
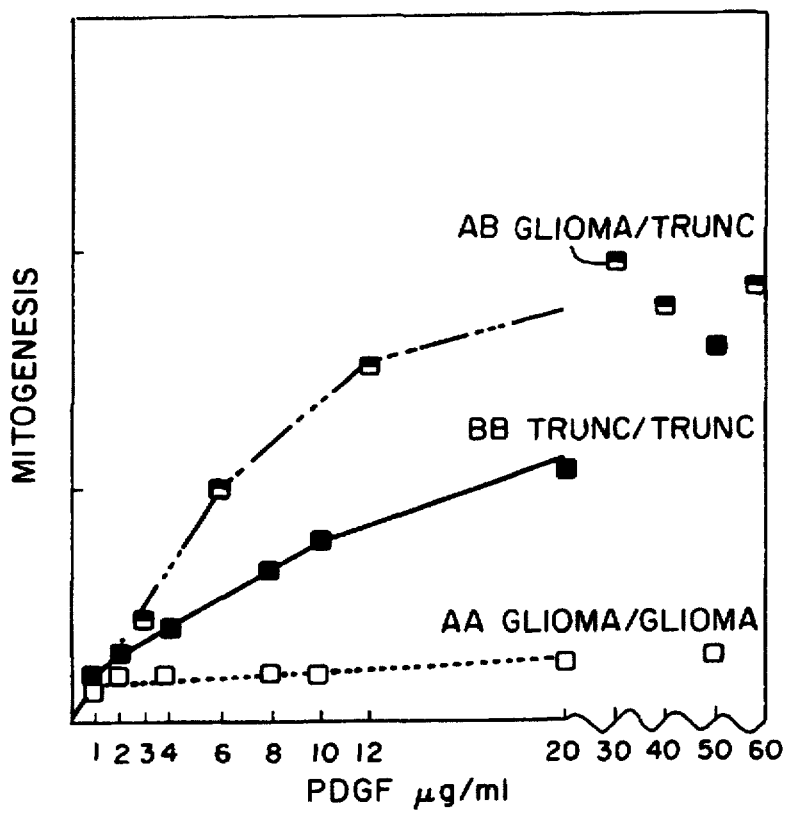
Figure 17B:
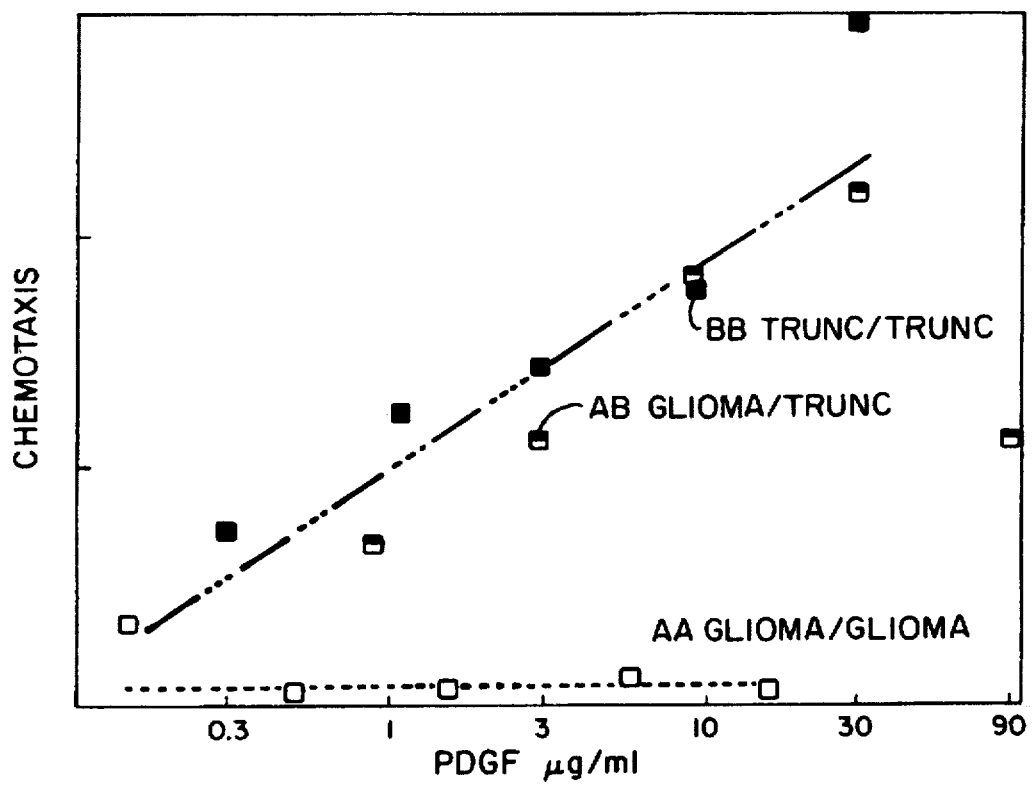
Figure 18:
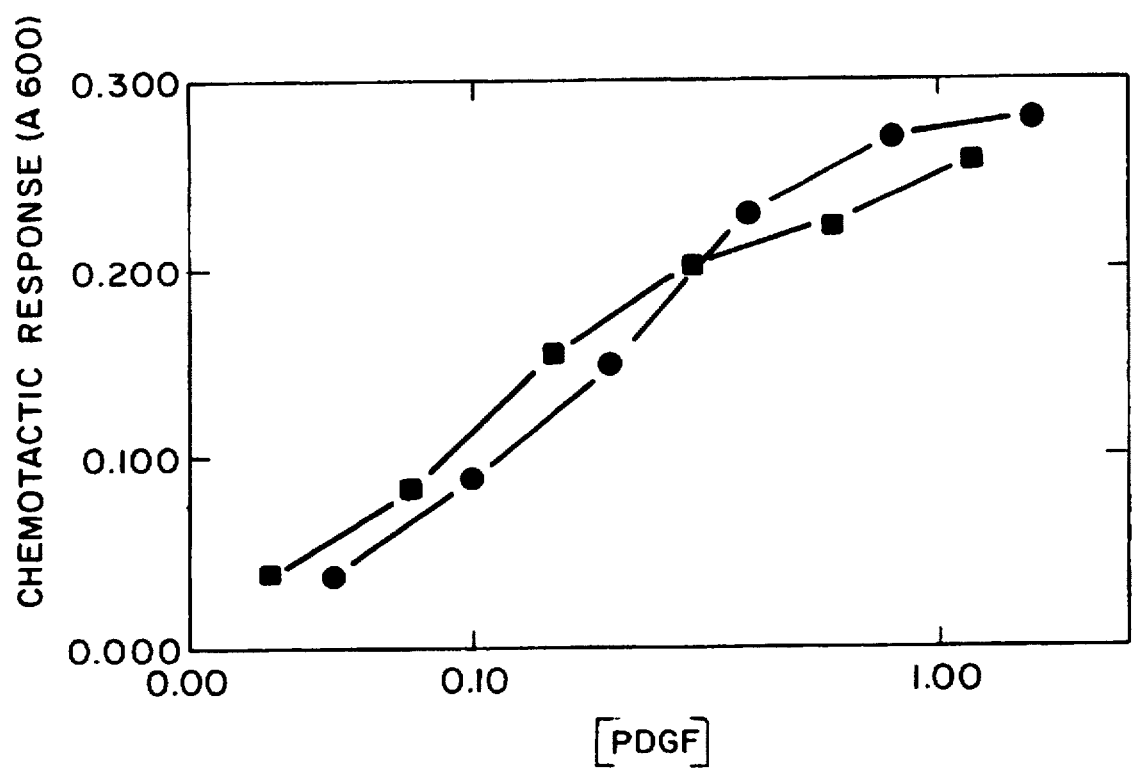
FIG. 18 is a graphic comparison of the chemotactic activity of platelet- and bacterially-produced forms of PDGF.

FIGS. 13–17 summarize chemotaxis and mitogenesis data for various species of PDGF or PDGF-like materials produced in accordance with the invention. In each graph, activity is plotted versus concentration (in μg/ml). FIG. 13 compares the activity of BB and AA homodimers. As illustrated, the Bc-sis homodimers are most active, and A-glioma homodimers least active. FIG. 14 illustrates the activity of BB (native) homodimers as compared with homodimers of the truncated B analogs and the Ala-Val B chain muteins. As illustrated, mitogenesis is decreased for the analog forms, but chemotaxis appears to be substantially identical to the native form. FIG. 15 illustrates a comparison of the activity of AB heterodimers (A/B endo/c-sis and AB glio/truncated). FIG. 16 illustrates a comparison of the activities of BB, AB, and AA dimers made from B-c-sis and A-endo. FIG. 17 illustrates a comparison of BB, AB, and AA dimers made from B-trunc and A-glial. Lastly, FIG. 18 illustrates a comparison of the chemotactic activity of platelet and recombinant derived AB heterodimers.

The invention may be embodied in other specific forms. What is claimed is:

1. A method of producing a biosynthetic, biologically active, PDGF species, said method comprising the steps of:
   (a) expressing in a prokaryote DNA comprising first, second, and third nucleotide sequences, said first nucleotide sequence including a promoter/operator region operable in a prokaryote, said second nucleotide sequence encoding a first polypeptide having an amino acid sequence sufficiently duplicative of a chain of a PDGF dimer to allow possession of the biological properties of causing mitogenic or chemotactic activity in fibroblasts after oxidation in the presence of a second PDGF chain to form a synthetic PDGF dimer, and said third nucleotide sequence encoding a leader polypeptide, the third sequence being interposed between and operably linked with the first and second sequences so as to be expressible as a fused polypeptide;
   (b) cleaving said fused polypeptide to produce said first polypeptide;
   (c) combining in vitro said first polypeptide and a second polypeptide comprising a chain of a PDGF dimer; and
   (d) refolding and oxidizing in vitro said first and second polypeptides to produce a biologically active, dimeric, PDGF species.

2. The method of claim 1 wherein step (a) is conducted in *E. coli*.

3. The method of claim 1 wherein the amino acid sequence of said first polypeptide is substantially homologous with an A chain of a PDGF dimer.

4. The method of claim 1 wherein the amino acid sequence of said first polypeptide is substantially homologous with a B chain of a PDGF dimer.

5. The method of claim 1 wherein the amino acid sequence of said first polypeptide comprises a $Ser_1$- $Ala_1$ mutein of a B chain of a PDGF dimer.

6. The method of claim 1 or 5 wherein the amino acid sequence of said first polypeptide comprises a Met 12→Val12 mutein of a B chain of a PDGF dimer.

7. The method of claim 1 wherein the amino acid sequence of said first polypeptide comprises a truncated analog of a B chain of a PDGF dimer.

8. The method of claim 1 wherein said second polypeptide is produced by conducting said steps (a) and (b).

9. The method of claim 1 wherein said DNA expressed in step (a) comprises a codon specifying a Met residue linking said first and leader polypeptides, and step (b) is conducted by cleaving said fused polypeptide with cyanogen bromide.

10. The method of claim 1 wherein step (d) comprises the step of contacting said first and second polypeptides with a physiologically compatible oxidizing solution which causes the formation of disulfide bonds between sulfhydryl group-containing amino acids of said polypeptides to produce biologically active, dimeric PDGF.

11. The method of claim 10 wherein step (d) further comprises the step of contacting said first and second polypeptides with a solution containing oxidized glutathione and reduced glutathione, said solution having a pH in the range of about 7.0 to 8.0.

12. The method of claim 11 wherein said reduced glutathione and oxidized glutathione are present in said solution at a ratio of about 10:1.

13. The method of claim 12 wherein said reduced glutathione is present at a concentration of about 1.0 mM, and said oxidized glutathione is present at a concentration of about 0.1 mM.

14. The method of claim 1 wherein one of said first and second polypeptides is the glioma species of an A chain of PDGF and the other is a B chain of PDGF, and wherein an excess of said glioma species is present in steps (c) and (d), said method resulting in an active PDGF heterodimer.

15. The method of claim 1 wherein one of said first and second polypeptides is the endothelial species of an A chain of PDGF and the other is a B chain of PDGF, and wherein an excess of the B chain of PDGF is present in steps (c) and (d), said method resulting in an active PDGF heterodimer.

* * * * *